(12) United States Patent
Moriya

(10) Patent No.: US 7,626,698 B2
(45) Date of Patent: Dec. 1, 2009

(54) METHOD OF ANALYSIS IN OPTICAL MEASUREMENTS

(75) Inventor: Naoji Moriya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/281,097

(22) PCT Filed: Feb. 28, 2006

(86) PCT No.: PCT/JP2006/303791

§ 371 (c)(1),
(2), (4) Date: Aug. 28, 2008

(87) PCT Pub. No.: WO2007/099615

PCT Pub. Date: Sep. 7, 2007

(65) Prior Publication Data

US 2009/0128809 A1    May 21, 2009

(51) Int. Cl.
G01N 15/02 (2006.01)
G01N 21/17 (2006.01)
G01N 27/447 (2006.01)
B05D 1/04 (2006.01)

(52) U.S. Cl. .................. 356/335; 356/334; 204/450; 427/78; 427/10

(58) Field of Classification Search ......... 356/335–343, 356/36–38, 305, 312, 328, 334; 204/450, 204/600; 427/10, 78, 123, 125; 436/514
See application file for complete search history.

(56) References Cited

U.S. PATENT DOCUMENTS 6,060,113 A * 5/2000 Banno et al. .................. 427/78
6,193,866 B1 * 2/2001 Bader et al. ................. 204/450
6,537,829 B1 * 3/2003 Zarling et al. ............... 436/514
2008/0049213 A1 * 2/2008 Wada ........................... 356/36
2008/0192252 A1 * 8/2008 Moriya et al. ............... 356/343

FOREIGN PATENT DOCUMENTS

JP        2005-181216 A    7/2005
WO    WO-2006/025158 A1    3/2006

OTHER PUBLICATIONS

International Search Report for the Application No. PCT/JP2006/303791 mailed Jun. 6, 2006.
Terazima, Masahide, "Translational Diffusion of Intermediate Species in Solutions", Research on Chemical Intermediates, 1997, vol. 23, No. 9, pp. 853-901.

(Continued)

*Primary Examiner*—Sang Nguyen
(74) *Attorney, Agent, or Firm*—Cheng Law Group, PLLC

(57) ABSTRACT

The method of the present invention generates a regularly lined electric field inside a container 1 retaining a sample formed by dispersing particle groups in a liquid by a voltage being applied to an electrode pair 2 provided in the container 1, generates a diffraction grating by a density distribution of the particle groups in the sample inside the container 1, and when acquiring a diffusion coefficient of particles from a temporal variation of intensity in a disappearing process of a diffracted light obtained by irradiating a beam of light to the diffraction grating generated by the density distribution of the particle groups, performs a particle size analysis of the particle groups by using an approximate analysis expression of a diffracted light attenuation, $I(t) = \propto \exp[-2q^2 Dt]$ which uses $q = 2\pi/\Lambda$ defined by a particle concentration modulation period $\Lambda$ in the density distribution diffraction grating of the particle groups, and the Einstein-Stokes relation. And if particle groups having a known particle size are dispersed in a liquid to be measured and similar measurements are performed, viscosity analysis of the liquid to be measured can be performed.

10 Claims, 8 Drawing Sheets

OTHER PUBLICATIONS

Wada, Yukihisa et al., "Yuden Eido O Mochiita Seitai Bunshi Kakusan Keisoku" ("Measurement of Biological Molecule Diffusion Speed Using Dielectrophoresis"), The Laser Society of Japan Gakujutsu Koenkai Dai 25 Kai Nenji Taikai Koen Yokoshu, Jan. 2005, p. 265, 21pII12.

Wada, Yukihisa et al., "Kato Kaisetsu Koshiho O Mochiita Nano Ryukei Keisoku Shuho No Kento" ("Nano-particle Measurements with Transient Grating Method"), 2005 Nen (Heisei 17 Nen) Shunki Dai 52 Kai The Japan Society of Applied Physics Kaikei Rengo Koenkai Koen Yokoshu, Separate vol. 3, Mar. 2005, p. 1142, 31p-ZF-21.

* cited by examiner

METHOD OF ANALYSIS IN OPTICAL MEASUREMENTS

TECHNICAL FIELD

The present invention relates to a method of analysis using an optical measuring apparatus that measures information of diffusion of particle groups in a sample formed by dispersing the particle groups movably in a medium by optical methodology; more specifically, it relates to a method of analysis in the optical measuring apparatus that measures a particle size of the particle groups or a viscosity of a liquid or gel, using a transient diffraction grating by a density distribution of the particle groups contained in the liquid or gel.

BACKGROUND TECHNOLOGY

In regard to the method of measuring information on diffusion of particle groups, the inventors of the present invention have proposed an apparatus and a method for evaluating the information on the diffusion of particles in a sample. That is, a container retains a sample in which particle groups are dispersed in a medium. A comb-type electrode pair has plural electrode pieces which are electrically connected at one ends thereof. The electrode pair is disposed in the container such that the other ends of electrode pieces of each electrode oppose each other with a minute gap. Applying voltage to the electrode pair generates electric field distribution regularly lined between the opposed electrode pieces to provide the particle groups in the sample inside the container with a dielectrophoretic force. Density distribution of the particle groups caused by the dielectrophoretic force generates a diffraction grating. After the diffraction grating is generated, the application of voltage to the electrode pair is stopped to diffuse the particle groups and then the diffraction grating is disappeared. Irradiating a beam of light to an area where the diffraction grating is generated in the container and detecting intensity of the obtained diffracted light between the generation and the disappearance of the diffraction grating. And information on the diffusion of particles in the sample is evaluated from a temporal variation of intensity of the diffracted light in disappearing process of the diffraction grating.

Further, the inventors widen width (length) of a diffraction grating generated by density distribution of particle groups in order that more components of the diffracted light may be contained in detected light without narrowing irradiation light to enhance sensitivity in measurements. And they propose also an electrode pattern for applying voltage to induce dielectrophoresis of particles by which diffracted light by diffraction grating generated by particle density can be measured separately from diffracted light by the electrode pattern (for example, refer to 'the examination of nano-particle measuring method using a transient diffraction grating' by Yukihisa Wada et al in the Proceedings of the 52nd spring meeting of the Japan Society of Applied Physics, separate Vol. 3 29 Mar. 2005, page 1142,31p-ZF-21. of the 52nd OYO BUTURIGAKU KANKEI RENGO).

In concrete, a sample to be measured formed by dispersing particle groups in a liquid or gel is retained in a container 1 as shown in a vertical section of FIG. 6 and a predetermined voltage is applied to an electrode pair 2 provided inside the container 1 to induce dielectrophoresis of the particle groups and thereby generate a diffraction grating by a density distribution thereof. A pattern illustrated in FIG. 7 is used as the electrode pair 2, and it consequently becomes possible to measure a diffracted light by the particle density diffraction grating separately from a diffracted light by the electrode pair 2.

As illustrated in FIG. 7, the electrode pair 2 is composed of electrodes 21 and 22. The electrode 21 is composed of plural parallel electrode pieces 21a and a connection area 21b that electrically connects the electrode pieces 21a. And the electrode 22 is composed of plural parallel electrode pieces 22a and a connection area 22b that electrically connects the electrode pieces 22a. The teeth of comb-electrodes belonging to 21 and 22 side are arranged as 21a-21a-22a-22a-21a-21a-22a-22a-and so on, as in FIG. 7. Two linear electrode pieces 21a or 22a are adjacently arrayed in the electrode area. There is no electrode piece in the non-electrode area. Two electrode pieces 21a or 22a of the electrode area are disposed in the non-electrode area of other electrode. As a whole two electrode pieces 21a and 22a are alternately disposed in parallel with a constant gap.

When an alternate voltage for example is applied between the electrodes 21 and 22, an electric field distribution corresponding to the electrode pattern is formed in the sample inside the container 1 by the electrode pattern. And the particle groups inside the sample are moved by the dielectrophoresis based on the electric filed distribution to generate a density distribution of the particle groups. In the electrode pattern illustrated in FIG. 7, a high-density area P of the particles is formed in an area where reverse polarity electrode pieces are adjacent. And the grating gap of the diffraction grating formed by the high-density area P of the particles consequently becomes twice as wide as the grating gap of the diffraction grating formed by the electrode pieces 21a or 22a. And the grating constants are as a result different between them. Diffracted light from the diffraction grating formed by the density distribution of the particle groups is defined to be diffracted light of a specific order by grating constant of the diffraction grating by the density distribution and grating constant of the diffraction grating by the electrode pieces. The diffracted light of a specific order appears in direction where the diffracted light by the diffraction grating formed by the electrode pieces does not exist.

In the example of FIG. 7, the diffracted light of [2m+1] order (m: integral number) by the diffraction grating formed by the density distribution of the particles appears in the direction where the diffracted light by the diffraction grating formed by the electrode pieces does not exist. If a detection optical system is located in the direction, background light contained in detected light by the detection optical system becomes background light composed of a scattered light and so forth. And background noise is accordingly kept low and it becomes possible to measure the diffracted light from the diffraction grating by the density distribution of the particle groups under a satisfactory background noise.

DISCLOSURE OF THE INVENTION

Problems to be Solved by the Invention

Now, the above method that the inventors have proposed obtains the information on the diffusion of particle groups from a temporal variation of intensity of a diffracted light in the disappearing process of a diffraction grating which is formed by generating a density distribution by electrically placing the particle groups unevenly distributed in the medium. And in case of analyzing a particle size of the particle groups or a viscosity of the liquid from this diffusion information, the calculation for obtaining the diffusion information from the temporal variation of intensity of the diffracted light requires complicated integral calculations, and it is necessary to presume particle size or liquid viscosity, for example, performing the pattern matching between actual measured data and attenuation pattern of intensity of the diffracted light obtained in advance by the calculation.

However, when the particles to be measured have a distribution in the particle size in this method, unfortunately it is difficult to separate influence of particle concentration inside the density diffraction grating to the temporal variation pattern of intensity of transient diffracted light from influence of the particle size distribution thereto.

The present invention is made in view of the above circumstances, developing the above techniques that the inventors have proposed, provides a method of analysis in the optical measurement, which facilitates the calculations for obtaining the diffusion information of particles in a sample from a temporal variation of intensity of a diffracted light in the disappearing process of a diffraction grating generated by a density distribution of particles. The method of analysis makes it possible to separate influence of distribution of the particle size of particle groups to be measured from the temporal variation of intensity of the diffracted light to realize a further precise analysis, and to shorten the time required for the multivariate analysis in the particle size analysis owing to the benefit of simplified analysis equations, and so forth.

Means to Solve the Problems

In order to solve the above problems, a method of analysis in an optical measuring method according to first aspect of the present invention, wherein the optical measuring method uses an apparatus comprising: a container that retains a gel sample or a liquid formed by dispersing particle groups movably in a medium; a power supply that generates a voltage with a predetermined pattern including a direct current, frequency modulation and voltage modulation, or pattern capable of being arbitrarily set; an electrode pair provided in the container, which generates a regularly lined electric field distribution in the container by applying the voltage from the power supply; a control means that controls application of the voltage from the power supply to the electrode pair to control generation of a diffraction grating generated by density distribution of particle groups in the sample inside the container generated by dielectrophoretic force acting on the particle groups and disappearance thereof; a light source that irradiates beam of light to an area where the diffraction grating is generated inside the container; and a photo-detector that detects diffracted light of the beam of light by the diffraction grating, the optical measuring method performing a particle size analysis of the particle groups in the sample from a temporal variation of intensity of a diffracted light detected by the photo-detector, wherein the method of analysis comprises the step of: using the Einstein-Stokes relation, $$D=K_B T/3\pi\eta d,$$

wherein $K_B$ is a Boltzmann constant as a diffusion coefficient, T is an absolute temperature of the particle-dispersed liquid to be measured, $\eta$ is a viscosity of the particle-dispersed liquid or the gel to be measured, and d is a particle size of the particles to be measured, and an approximate analysis expression of a diffracted light attenuation, $$I(t)=\propto \exp[-2q^2 Dt],$$

which uses $q=2/\Lambda$ defined by a particle concentration modulation period $\Lambda$ in the diffraction grating generated by density distribution of the particle groups to obtain the particle diameter d.

A method of analysis in an optical measuring method according to second aspect of the present invention, wherein the optical measuring method uses an apparatus comprising: a container that retains a gel or a sample liquid formed by dispersing particle groups with known particle size movably in a medium; a power supply that generates a voltage with a predetermined pattern including a direct current, frequency modulation and voltage modulation, or pattern capable of being arbitrarily set; an electrode pair provided in the container, which generates a regularly lined electric field distribution in the container by applying the voltage from the power supply; a control means that controls application of the voltage from the power supply to the electrode pair to control generation of a diffraction grating generated by density distribution of particle groups generated by dielectrophoretic force acting on particles in a suspension inside the container and disappearance thereof; a light source that irradiates beam of light to an area where the diffraction grating is generated inside the container; and a photo-detector that detects diffracted light of the beam of light by the diffraction grating, the optical measuring method performing a viscosity analysis of the sample liquid and gel from a temporal variation of intensity of a diffracted light detected by the photo-detector, wherein the method of analysis comprising the step of: using the Einstein-Stokes relation, $$D=K_B T/3\pi\eta d,$$

wherein $K_B$ is a Boltzmann constant as a diffusion coefficient, T is an absolute temperature of the sample liquid or gel to be measured, $\eta$ is a viscosity of the sample liquid or gel to be measured, and d is a known particle size of the particles, and an approximate analysis expression of a diffracted light attenuation, $$I(t)=\propto \exp[-2q^2 Dt],$$

which uses $q=2\pi/\Lambda$ defined by a particle concentration modulation period $\Lambda$ in the diffraction grating generated by density distribution of the particle groups to obtain the viscosity $\eta$ of the sample liquid or gel.

In the first and second aspect of the present invention, it is preferable to adopt any one of the following methods.

One method (third aspect of the present invention) further comprise the step of: measuring a plurality of samples having various concentrations under same dielectrophoretic condition in the measurement; comparing the measurement results to extract a concentration condition in which a phase modulation amplitude of the diffraction grating generated by the density distribution of the particle groups with respect to incident light is smaller than 1 and an amplitude modulation amplitude thereof is smaller than 1; and applying the approximate analysis expression of the diffracted light attenuation to the result measured under the extracted concentration condition.

Another method (fourth aspect of the present invention) further comprise the step of: applying the approximate analysis expression of the diffracted light attenuation to a diffracted light signal only in a time domain in which a phase modulation amplitude of the diffraction grating generated by the density distribution of the particle groups with respect to incident light is smaller than 1 and an amplitude modulation amplitude thereof is smaller than 1. Further, according to another method (fifth aspect of the present invention), the measurement may be performed under an voltage application time for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

Furthermore, according to another method (sixth aspect of the present invention), the measurement may be performed under an application voltage for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

The approximate analysis expression of the attenuation of intensity of a diffracted light used in the method of the present invention will be derived hereunder.

When the electrode pattern illustrated in FIG. 7 is used and a diffraction grating by a density distribution of particle groups in the sample is generated, a diffusion equation is examined wherein z-axis is a height direction of the particle collection area (high-density area P), y-axis is a groove direction of the diffraction grating, and x-axis is the disposition direction of the grooves as illustrated in FIG. 1.

In this case, the diffusion equation can be expressed by following formula (1), wherein a particle concentration profile function is expressed by u(x, y, z, t).

[Formula 1]

$$\frac{\partial u(x, y, z, t)}{\partial t} = D_x \cdot \frac{\partial^2 u(x, y, z, t)}{\partial x^2} + D_y \cdot \frac{\partial^2 u(x, y, z, t)}{\partial y^2} + D_z \cdot \frac{\partial^2 u(x, y, z, t)}{\partial z^2} \quad (1)$$

However, since the diffusion is an isotropic phenomenon, each diffusion coefficient is equal; a following formula 2 is derived from the Einstein-Stokes relation.

[Formula 2]

$$D_x = D_y = D_z \equiv D = \frac{k_B T}{3\pi\eta d} \quad (2)$$

wherein $k_B$ is Boltzmann constant, T is an absolute temperature, $\eta$ is a viscosity of a liquid, and d is a particle size of a particle.

In a diffraction grating of particles that are collected and formed by the dielectrophoresis, because the y-axis direction is sufficiently long compared with the x-axis direction representing a width of the diffraction grating and the y-axis direction representing a height thereof, it is conceivable that the diffusion is limited to appear on the upper side of a plane where the grating is formed and in the groove-width direction, and the y-variables can be consequently omitted. The following formula can be acquired as a result.

[Formula 3]

$$\frac{\partial u(x, z, t)}{\partial t} = D \cdot \left[ \frac{\partial^2 u(x, z, t)}{\partial x^2} + \frac{\partial^2 u(x, z, t)}{\partial z^2} \right] \quad (3)$$

And if a probe beam of light enters substantially vertically, a diffusion of particles to the z-axis which is the height direction of the grating does not have influence on formation of phase difference and variation of transmittance as the grating, and the temporal variation of the z-axis direction can be consequently neglected, and the above diffusion equation can be finally expressed by the following diffusion equation, with only one axis direction.

[Formula 4]

$$\frac{\partial u(x, t)}{\partial t} = D \cdot \frac{\partial^2 u(x, t)}{\partial x^2} \quad (4)$$

Hereunder, a solution method of separation of variables of the diffusion equation is used. The separation of valuables is applied to time and space of a concentration distribution function, and the following formula is defined.

[Formula 5]

$$u(x,t)=X(x)\cdot T(t) \quad (5)$$

Here, since the initial density distribution at t=0 is periodical, given that $\Lambda$ is the grating period, the following formula is obtained.

[Formula 6]

$$X(x+\Lambda)=X(x) \quad (6)$$

And since a term of time concerning the diffusion is to converge on the steady state in case of t→∞, the following formula is obtained.

[Formula 7]

$$\lim_{t \to \infty} T(t) = \text{Const.} \quad (7)$$

Solution of variable separation that applies to the conditions of the above formula (6) and formula (7) can be expressed as the following formula (8), as is well known.

[Formula 8]

$$u(x, t) = C_n\{1 + \cos(n \cdot q \cdot x)\} \cdot \exp[-n^2 \cdot q^2 D \cdot t] \quad (8)$$
$$= \{C_n \cdot \exp[-n^2 \cdot q^2 D \cdot t]\} \cdot \{1 + \cos(n \cdot q \cdot x)\}$$

wherein, $C_n$ is an initial density amplitude, n is a positive integral number, and q is given by the following formula (9) using the grating period $\Lambda$.

[Formula 9]

$$q = \frac{2\pi}{\Lambda} \quad (9)$$

Since the diffusion equation (4) is linear, if there are plural solutions Um(x, t), a linear combination thereof is also a solution. And the formula (8) can be expanded as a result in the following as a general solution.

[Formula 10]

$$u(x, t) = \sum_{n=1}^{\infty} \{C_n \cdot \exp[-n^2 \cdot q^2 D \cdot t]\} \cdot \{1 + \cos(n \cdot q \cdot x)\} \quad (10)$$

The above consideration has been made on the premise that the density distribution function of particles has a simple cosine profile. However an actual density distribution profile is a periodical function of the period Λ, but the actual density distribution profile is not considered to be a simple trigonometric function. However, according to Fourier, any periodical function can be expanded by a Fourier series. The density function P(x) having a periodicity of an interval [−Λ/2, Λ/2] being symmetrical with respect to the origin can be expanded by the Fourier series as follows.

[Formula 11]

$$P(x) = a_0 + \sum_{n=1}^{\infty} \{a_n \cdot \cos[n \cdot q \cdot x] + b_n \cdot \sin[n \cdot q \cdot x]\} \quad (11)$$

$$a_0 = \frac{1}{2\pi} \int_{-\frac{\Lambda}{2}}^{\frac{\Lambda}{2}} P(x)$$

$$a_n = \frac{1}{\pi} \int_{-\frac{\Lambda}{2}}^{\frac{\Lambda}{2}} P(t) \cos(n \cdot q \cdot t) dt$$

$$b_n = \frac{1}{\pi} \int_{-\frac{\Lambda}{2}}^{\frac{\Lambda}{2}} P(t) \sin(n \cdot q \cdot t) dt = 0$$

Here, comparing the formula (10) and the formula (11) in case of t=0 representing an initial density in the formula (11) easily finds that the formula (11) is equivalent to the formula (10). And the diffusion density profile function P(x,t) of the particle density grating formed by the dielectrophoresis can be expressed as a result by the formula (12).

[Formula 12]

$$P(x, t) = a_0 + \sum_{n=1}^{\infty} \{a_n \cdot \exp[-n^2 \cdot q^2 D \cdot t]\} \cdot \cos(n \cdot q \cdot x) \quad (12)$$

The formula (12) forms a linear combination of an n-order higher harmonic cosine function, wherein the periodical pitch Λ of a high-density particle groups collected by the dielectrophoresis is a fundamental periodic function, whereas a attenuation coefficient of an amplitude of the n-order higher harmonic cosine function is $n^2$ times as great as a fundamental period. And the amplitude components of the n-order higher harmonic cosine function consequently reduce influence rapidly from a start of the diffusion. After a certain time except an extremely initial stage of the diffusion, the density profile function is influenced only by the fundamental periodical components, and is regarded approximately as follows.

[Formula 13]

$$P(x,t) \approx a_0 + a_1 \cdot \exp[-q^2 D \cdot t] \cdot \cos(q \cdot x) \quad (13)$$

If particle size is substantially a wavelength of a probe beam or less, contribution of particles to scattering is extremely low, and effect of refractive index that reflects an optical density of the particles themselves becomes dominant. And a refractive index variation of a liquid in which particles are dispersed, that is, a phase variation and an amplitude variation are proportional to the particle concentration. Since the particle density grating formed by the dielectrophoresis is considered to be about 10 μm or less with respect to transmission direction of light, a liquid having the concentration distribution expressed by the cosine function as the formula (13) is considered to be a thin grating giving a cosine phase/amplitude difference in case of a low order diffracted light having an insignificant diffraction angle.

And a coordinate system illustrated in FIG. 2 is used to calculate the diffracted light based on the Fraunhofer diffraction theory. An amplitude/phase transmittance of the density grating g(x) is given to the amplitude $U_m(f)$ of the diffracted light at a sufficiently far position in m-th phase/amplitude modulation period to become the following.

[Formula 14]

$$U_m(f) = C \int_{-\infty}^{\infty} g(x) \cdot \exp[-i \cdot k \cdot f \cdot x] dx \quad (14)$$

wherein, if a wavelength of a probe beam is λ, k=2π/λ (wave number) and f=ξ/L (direction of an observation point).

Further, influence by electrodes that control the dielectrophoresis is defined as FIG. 3 and the origin of the density diffraction grating is shifted to simplify later calculations, and the phase/amplitude modulation function is consequently expressed as a sine function.

[Formula 15]

$$P(x,t) \approx a_0 + a_1 \cdot \exp[-q^2 D \cdot t] \cdot \sin(q \cdot x) \quad (15)$$

If proportional coefficients representing a phase variation and an absorption coefficient variation with respect to a particle concentration is $\phi_0$, $\mu_0$ respectively, the formula (14) becomes the following using the formula (13).

[Formula 16]

$$U_m(f) = \quad (16)$$

$$A_m \int_{m\Lambda - \frac{w}{2}}^{m\Lambda + \frac{w}{2}} \exp[-\{i \cdot \phi_0 \cdot P(z, t) + \mu_0 \cdot P(x, t)\}] \cdot \exp[-ikfx] dx +$$

$$A_m \int_{(m+\frac{1}{2})\Lambda - \frac{w}{2}}^{(m+\frac{1}{2})\Lambda + \frac{w}{2}} \exp[-\{i \cdot \phi_0 \cdot P(z, t) + \mu_0 \cdot P(x, t)\}] \cdot \exp[-ikfx] dx$$

wherein, $A_m$ represents an amplitude of light that enters the m-th phase/amplitude modulation period.

If a shielding area by electrodes is considerably large, the density distribution P(x, t) being a reference of the phase/amplitude modulation of the density diffraction grating can be regarded as a simple time function as follows, since a density variation is small within a range of an aperture width w.

[Formula 17]

$$P(x, t) = \begin{cases} a_0 + a_1 \cdot \exp[-q^2 D \cdot t] = P_1(t) \ldots \frac{2\pi \cdot x}{\Lambda} \approx 2l\pi \\ a_0 - a_1 \cdot \exp[-q^2 D \cdot t] = P_0(t) \ldots \frac{2\pi \cdot x}{\Lambda} \approx (2l+1)\pi \end{cases} \quad (17)$$

The formula (16) consequently becomes the following.

[Formula 18]

$$U_m(f) = A_m \exp[\{-i \cdot \phi_o - \mu_0\} \cdot P_1(t)] \cdot \int_{m\Lambda - \frac{w}{2}}^{m\Lambda + \frac{w}{2}} \exp[-ikfx] dx + \quad (18)$$

$$A_m \exp[\{-i \cdot \phi_o - \mu_0\} \cdot P_0(t)] \cdot \int_{m\Lambda - \frac{w}{2}}^{m\Lambda + \frac{w}{2}} \exp\left[-ikf\left\{x + \frac{\Lambda}{2}\right\}\right] dx$$

Provided that the diffraction grating is uniformly illuminated ($A_m \equiv A$), if the formula (18) is superposed over the N-pieces continuous periodical intervals [0, N−1], an amplitude of the diffracted light is calculated as the sum of the contribution of [0,N−1] grooves shown as formula (18).

[Formula 19]

$$U(f) = A\left[\exp[\{-i\cdot\phi_o - \mu_0\}\cdot P_1(t)] + \exp[\{-i\cdot\phi_o - \mu_0\}\cdot P_0(t)]\cdot\exp\left[-\frac{ikf\Lambda}{2}\right]\right]\cdot F(f) \quad (19)$$

Here, F(f) is given by the following.

[Formula 20]

$$F(f) = \int_{-\frac{w}{2}}^{\frac{w}{2}} \exp[-ikfx]\,dx \sum_{m=0}^{N-1} \exp[-ikfm\Lambda] \quad (20)$$

And a term of temporal variation of amplitude of diffracted light is consequently understood to be only the following expression.

[Formula 21]

$$\exp[\{-i\cdot\phi_o - \mu_0\}\cdot P_1(t)] + \exp[\{-i\cdot\phi_o - \mu_0\}\cdot P_0(t)]\cdot\exp\left[-\frac{ikf\Lambda}{2}\right] \quad (21)$$

And the variation I(t) of intensity of first order diffracted light becomes as a result the following, using the condition of $kf\Lambda = 2\pi$.

[Formula 22]

$$I(t) \propto |\exp[\{-i\cdot\phi_0-\mu_0\}\cdot P_1(t)] - \exp[\{-i\cdot\phi_0-\mu_0\}\cdot P_0(t)]|^2 \quad (22)$$

Expanding this formula by using the formula (17) again, the formula (22) becomes as follows.

[Formula 23]

$$I(t) \propto \quad (23)$$

$$\left|\exp\left[\begin{array}{c}\{-i\cdot\phi_o - \mu_0\}\cdot\\ \{a_0 + a\cdot\exp[-q^2\cdot D\cdot t]\}\end{array}\right] - \exp\left[\begin{array}{c}\{-i\cdot\phi_o - \mu_0\}\cdot\\ \{a_0 - a\cdot\exp[-q^2\cdot D\cdot t]\}\end{array}\right]\right|^2 =$$

$$\left|\exp\left[\begin{array}{c}\{-i\cdot\phi_o - \mu_0\}\cdot\\ \{a\cdot\exp[-q^2\cdot D\cdot t]\}\end{array}\right] - \exp\left[\begin{array}{c}\{i\cdot\phi_o + \mu_0\}\cdot\\ \{a\cdot\exp[-q^2\cdot D\cdot t]\}\end{array}\right]\right|^2 =$$

$$2 + \exp[2\mu_0\cdot a\cdot\exp(-2\cdot q^2\cdot D\cdot t)] +$$

$$\exp[-2\mu_0\cdot a\cdot\exp(-2\cdot q^2\cdot D\cdot t)] -$$

$$4\cdot\cos^2[\phi_0\cdot a\cdot\exp(-2\cdot q^2\cdot D\cdot t)]$$

From the definition, $\phi_0\cdot a$ is a modulation amplitude of a electric field phase of the density diffraction grating, and $\mu_0\cdot a$ is a modulation amplitude of a electric field amplitude of the density diffraction grating; rewriting the above two into $\phi, \mu$, respectively, and executing the Taylor Expansion to the formula (23) until a second-order term under a condition of $\phi, \mu \ll 1$ will produce the following.

[Formula 24]

$$I(t) \propto 4\cdot\{\phi^2 + \mu^2\}\cdot\exp[-2\cdot q^2\cdot D\cdot t] \quad (24)$$

Eventually, the formula (24) can be written as follows.

[Formula 25]

$$I(t) \propto \exp[-2\cdot q^2\cdot D\cdot t] \quad (25)$$

Consequently, if an amplitude of a sinusoidal modulation of the phase and amplitude of an incident light electric field generated by the density diffraction grating satisfies the condition of $\phi, \mu \ll 1$, the diffracted light attenuates exponentially. And, in case of measuring monodispersed particle groups and making a logarithmic expression of the intensity of diffracted light, the temporal variation of the intensity of diffracted light becomes a straight line. If the intensity of diffracted light deviates from the straight line, it is easily inferred that particle group has a particle size distribution.

As described above, according to the first and second aspect of the present invention, the diffusion coefficient D of the particles in the sample can be calculated by a comparably simple calculation using the formula (25) from the temporal variation I(t) of the intensity of diffracted light in the disappearing process of the diffraction grating generated by the density distribution of the particle groups.

However, in order to calculate a precise diffusion coefficient D by the formula (25), it is necessary to satisfy the condition of $\phi, \mu \ll 1$ as described above. Concretely, to satisfy this condition, the particle concentration in the sample needs to avoid being excessively high (the third aspect of the present invention).

Or, it is necessary to avoid measuring the diffracted light in a state that the particle concentration in the high density area of particles is excessively high. Concretely, it is necessary to use measurement data in a state that the particle groups start to diffuse to some extent to avoid measuring the temporal variation of the intensity of diffracted light in a state that the particle density of the diffraction grating formed by collecting the particles by the electric field is over a limitation (the fourth aspect of the present invention), or it is necessary to avoid applying a voltage to the electrode pair for excessively long time for not excessively collecting the particles before starting to measure the intensity of diffracted light (the firth aspect of the present invention), or it is necessary to avoid excessively raising a voltage applied to the electrode pair for not excessively collecting the particles before starting to measure the intensity of diffracted light (the sixth aspect of the present invention).

To confirm whether the above concrete conditions are satisfied, the measurement is performed while any one of the conditions are changed. For example, the measurement is performed under plural particle concentrations. If characteristic in a disappearing process of the diffracted light of one concentration does not meet the characteristic of other concentrations in a side of strong dielectrophoretic condition, it is possible to easily understand that a measurement result of the concentration does not meet the conditions.

BRIEF DESCRIPTION OF THE DRAWINGS

FIG. 9 is a graph illustrating an example of a temporal variation of the intensity of diffracted light in the disappearing process of the density distribution diffraction grating measured by using the method for analyzing particle size in the optical measuring method of the present invention (attenuation characteristic of diffracted light), in which

DESCRIPTION OF THE SYMBOLS

Figure 1:
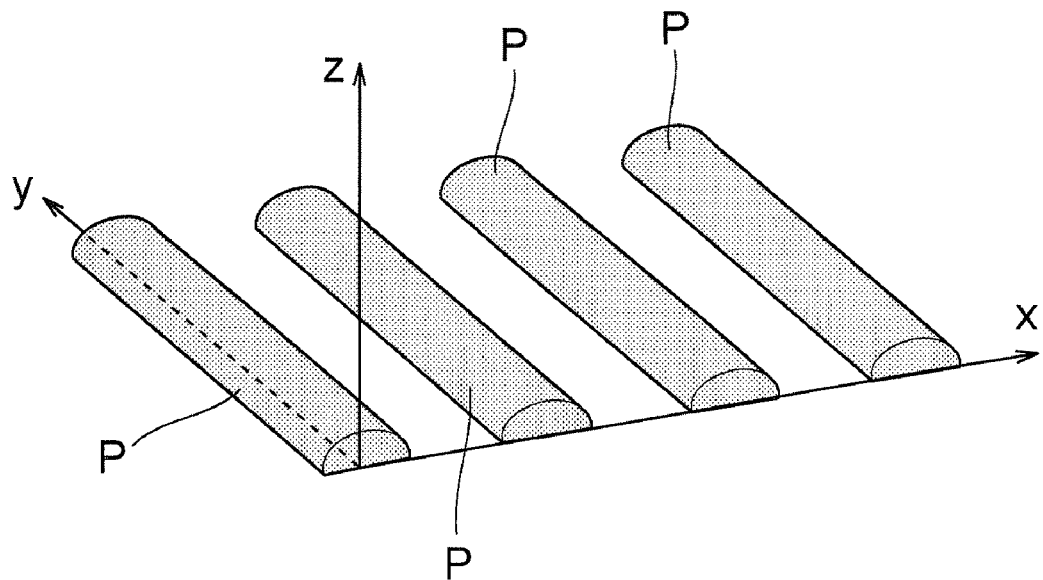
FIG. 1 is an explanatory chart of the coordinate system, for deriving the approximate analysis expression of the attenuation of a diffracted light in the method of the present invention.
Figure 2:
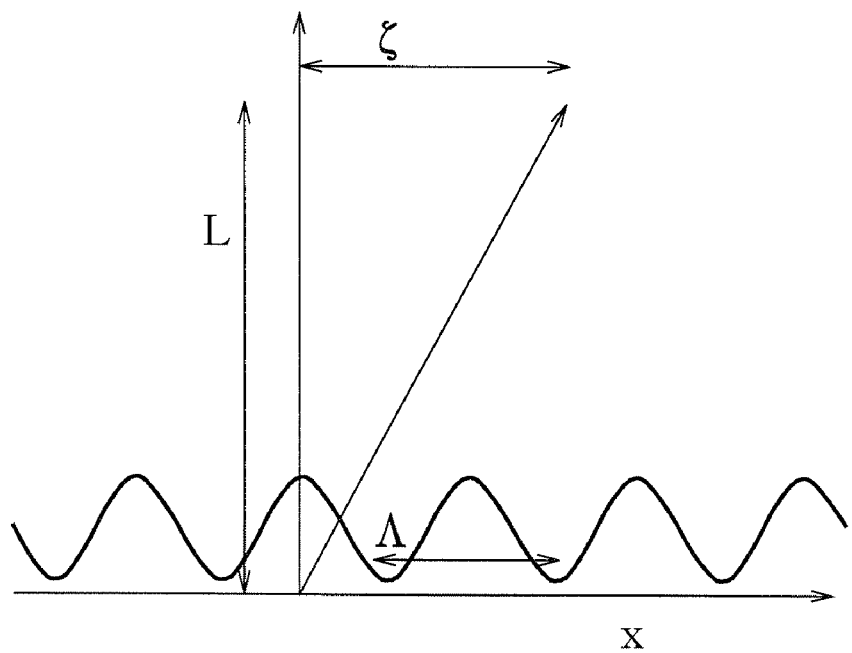
FIG. 2 is similarly an explanatory chart of the coordinate system, for deriving the approximate analysis expression of the attenuation of a diffracted light in the method of the present invention.
Figure 3:
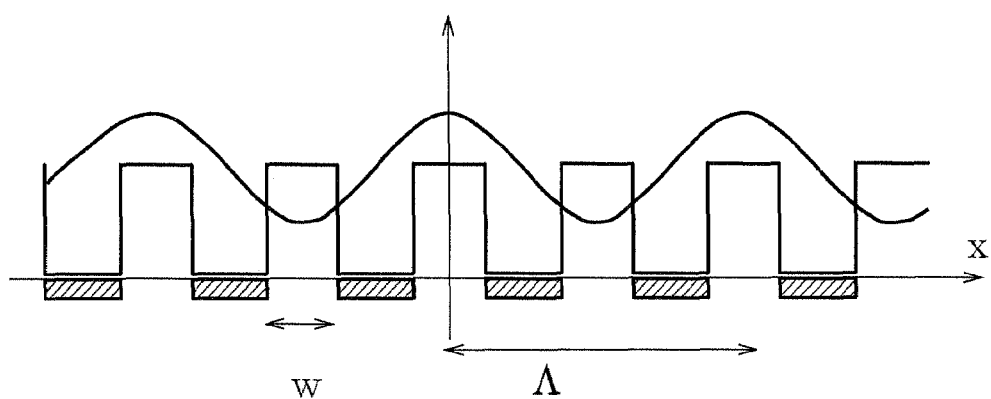
FIG. 3 is similarly an explanatory chart of the profile of the density diffraction grating, for deriving the approximate analysis expression of the attenuation of a diffracted light in the method of the present invention.

1: container
2: electrode pair
21, 22: electrode
21a, 22a: electrode piece
21b, 22b: connection area
3: power supply for electrodes
4: irradiation optical system
5: detection optical system
6: device for controlling apparatus and loading and processing data

BEST MODE FOR CARRYING OUT THE INVENTION

The best mode for carrying out the invention will be described hereunder with reference to the appended drawings. Now, the present invention is not confined to the mode described hereunder, and naturally the invention includes various modes without a departure from the spirit of the invention. Further, dielectrophoretic force is explained by positive dielectrophoretic force that collects particles by an attractive force in the description hereunder. However, negative dielectrophoretic force having a repulsive force may form a particle density modulation by which the particle density becomes lower in the vicinity of the electrode than the periphery thereof. The particle density modulation may function as a diffraction grating as well.

Figure 4:
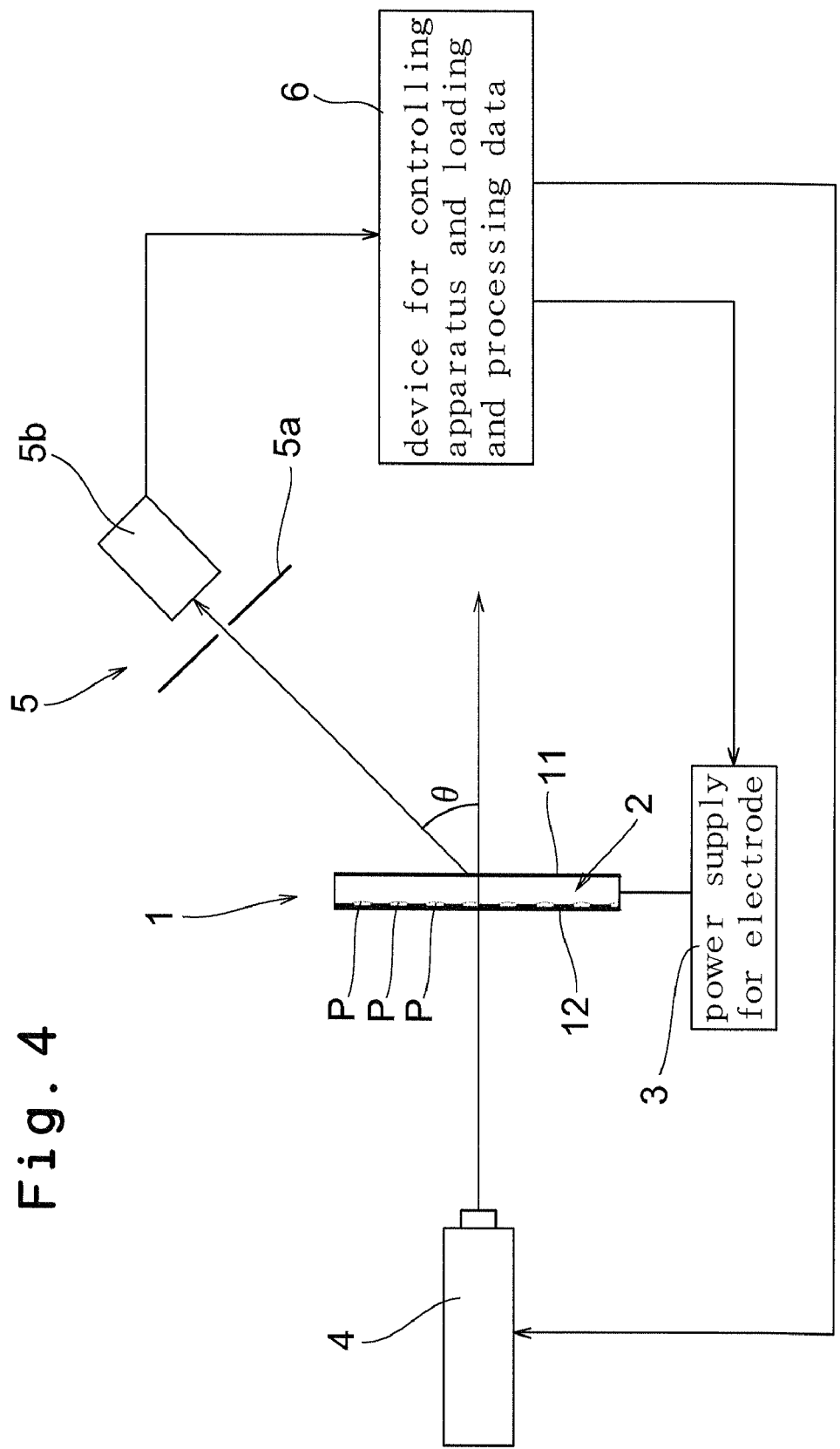
FIG. 4 is a configuration diagram of an embodiment of the present invention, which shows both a typical chart illustrating an optical configuration and a block diagram illustrating an electric configuration.

The measuring apparatus mainly includes, as illustrated in FIG. 4, a container 1 that retains a sample in which particle groups are movably dispersed in a medium, for example, a sample in which particles are dispersed in a liquid, or a sample in which particles are movably dispersed in a gel, an electrode power supply 3 that applies a voltage to an electrode pair 2 provided inside the container 1, an irradiation optical system 4 that irradiates a beam of light to the container 1, a detection optical system 5 that measures a diffracted light from a diffraction grating generated by a density distribution of the particle groups generated inside the container 1 by the voltage applied to the electrode pair 2, and a device 6 for controlling the apparatus and loading and processing data that controls the whole apparatus as well as loads data output from the detection optical system 5 to process the data.

Figure 5:
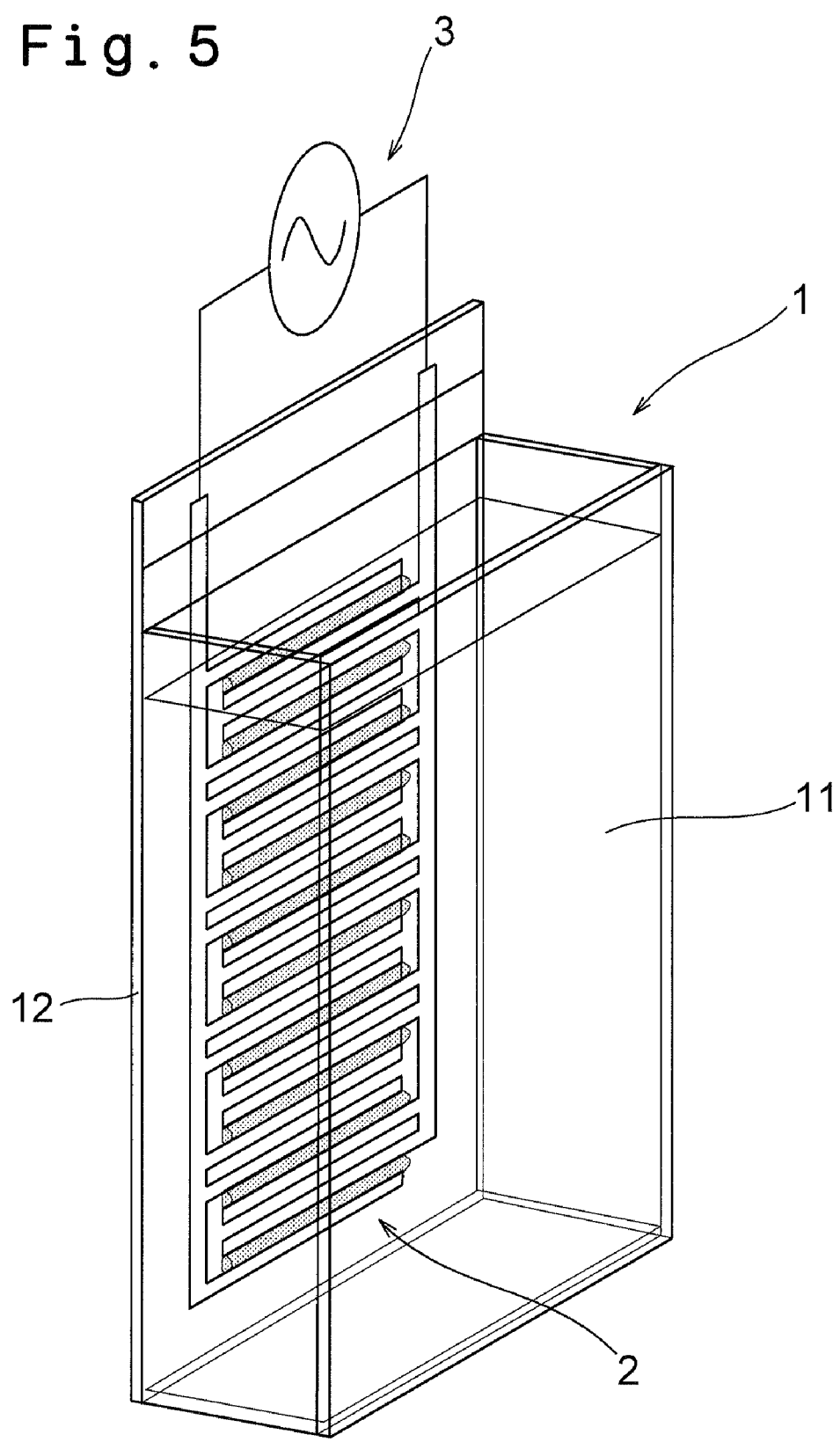
FIG. 5 is a chart showing both a perspective view illustrating a concrete example of the container 1 in FIG. 1 and a circuit diagram for applying a voltage to the electrode pair 2.
Figure 6:
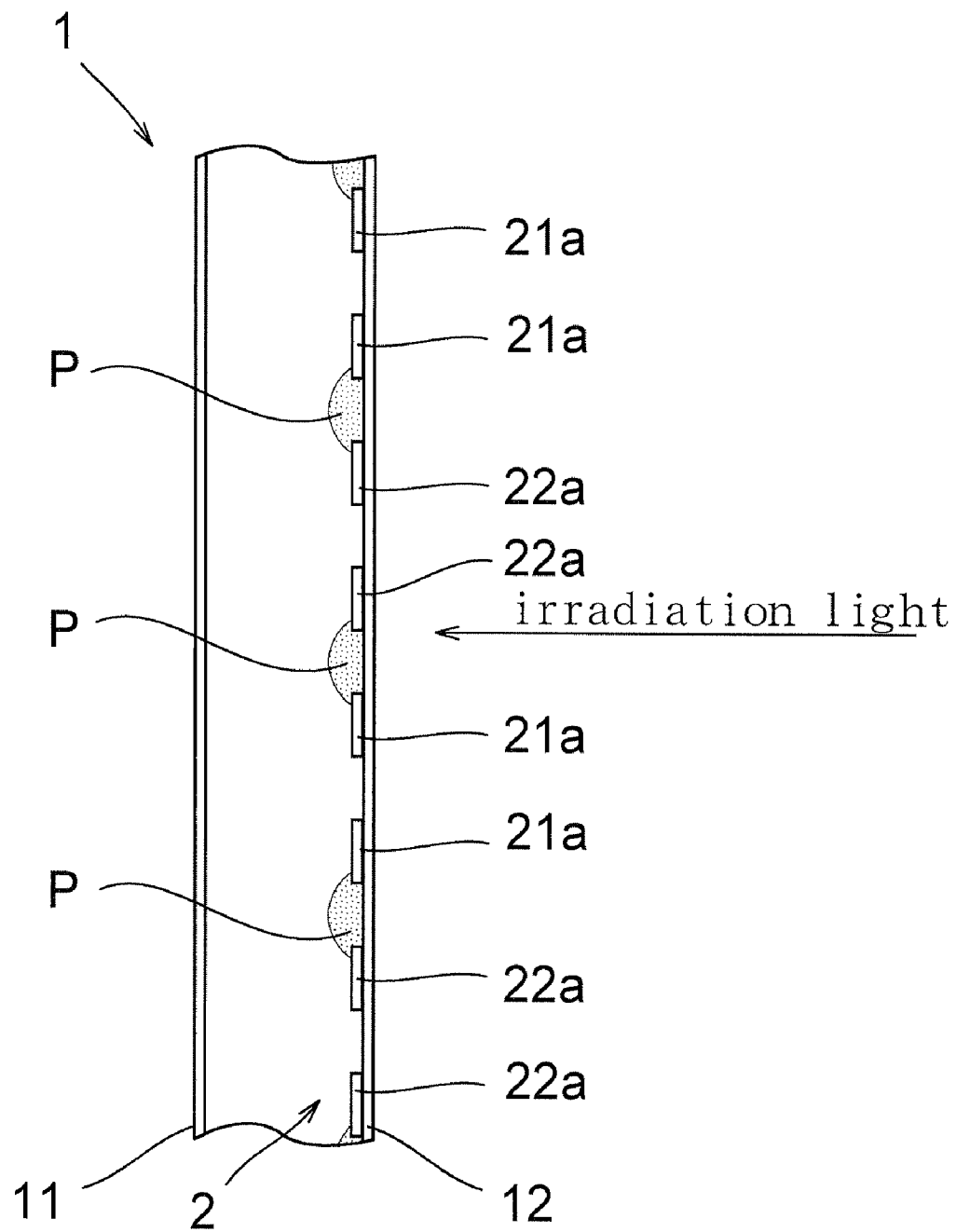
FIG. 6 is a typical partial section of the container 1 in FIG. 1.

The container 1 in this example has, as illustrated in FIG. 5 and FIG. 6, at least walls 11 and 12 arranged mutually in parallel and made of a transparent material And the electrode pair 2 is formed on the inner surface of the wall 12.

Figure 7:
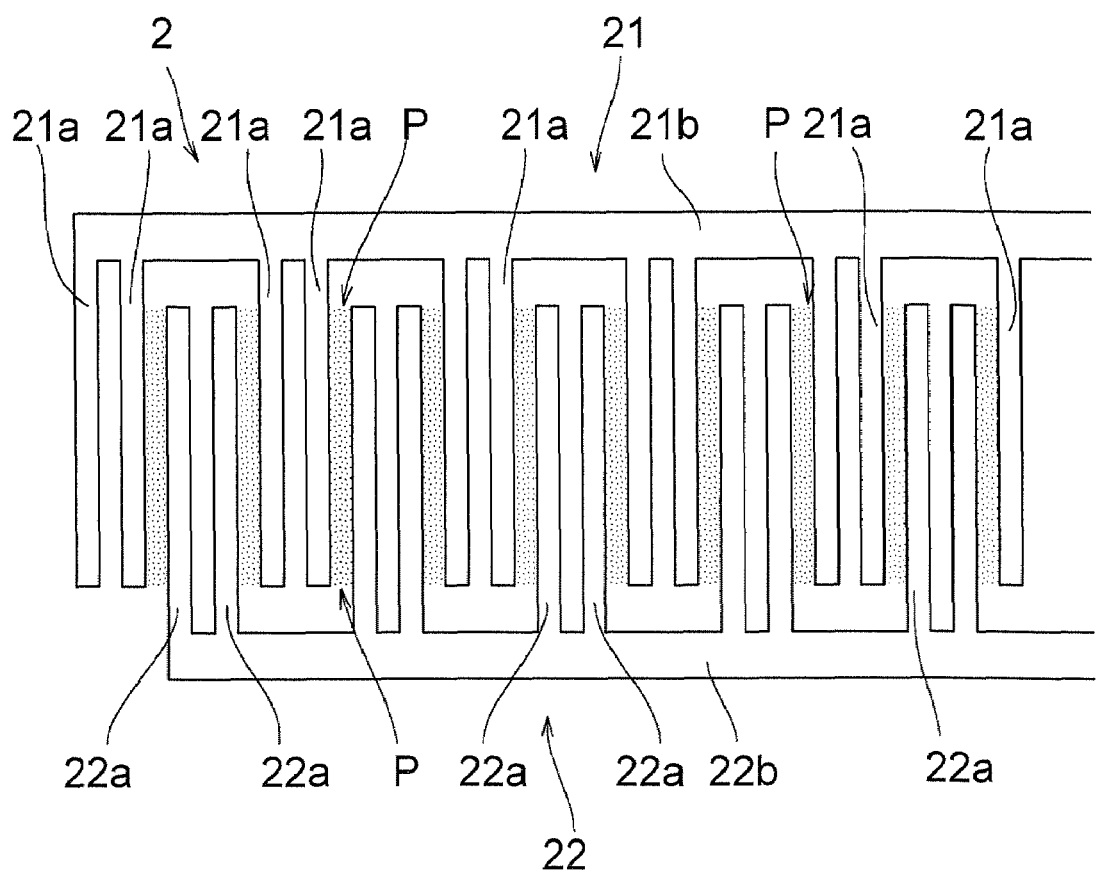
FIG. 7 is an explanatory chart of a pattern example for the electrode pair 2 provided inside the container 1 in the embodiment of the present invention.

As illustrated in FIG. 7, the electrode pair 2 is composed of electrodes 21 and 22. The electrode 21 is composed of plural parallel electrode pieces 21a and a connection area 21b that electrically connects the electrode pieces 21a. And the electrode 22 is composed of plural parallel electrode pieces 22a and a connection area 22b that electrically connects the electrode pieces 22a. The teeth of comb-electrodes belonging to 21 and 22 side are arranged as 21a-21a-22a-22a-21a-21a-22a-22a and so on, as in FIG. 7. Two linear electrode pieces 21a or 22a are adjacently arrayed in the electrode area. There is no electrode piece in the non-electrode area. Two electrode pieces 21a or 22a of the electrode area of are disposed in the non-electrode area of other electrode. As a whole two electrode pieces 21a and 22a are alternately disposed in parallel with a constant gap.

To the above electrode pair 2 is applied a voltage from the electrode power supply 3. And this applied voltage generates electric field distribution inside the sample retained in the container 1. The electric field distribution makes the particle groups in the sample migrate as described later to generate a diffraction grating by the density distribution of the particle groups. The output voltage from the electrode power supply 3, that is, the voltage applied to the electrode pair 2 is controlled by the device 6 for controlling the apparatus and loading and processing data, as described later.

The irradiation optical system 4 outputs substantially monochromatic beam of light shaped into substantially parallel beam of light. And the output beam is irradiated to a surface of the container 1 on which the electrode pair 2 is formed. The light source of the irradiation optical system 4 may be simple to emit only monochromatic light such as laser or LED. However, a quasi-monochromatic light; a beam of light emitted from a continuous wavelength light source and passing through a band-pass filter or a spectroscope, may be used. The spectrum bandwidth may be some ten nm or less in the visible wavelength region, for example.

The detection optical system 5 is disposed in emitted direction of diffracted light by the diffraction grating generated by the density distribution of the particle groups inside the container 1, for example in the emitted direction of first order diffracted light. The detection optical system 5 is made up with, for example, a pinhole 5a and a photo-detector 5b. The detection optical system 5 measures time-series variation of intensity of diffracted light by the diffraction grating generated by a density distribution of the particle groups inside the container 1. It should be noted that a condensing lens may be placed between the container 1 and the pinhole 5a.

Now in the above construction, if alternate voltage is applied between the electrodes 21 and 22 of the electrode pair 2, an electric field distribution corresponding to the electrode pattern is formed in the sample inside the container 1, and the density distribution of the particle groups is generated by the dielectrophoresis based on the field distribution. Concretely, high density regions P of the particles are formed in the areas where the electrode pieces of reverse polarity are adjacent in the electrode pair 2 illustrated in FIG. 7, that is, in the areas where the electrode pieces 21a of the electrode 21 and the electrode pieces 22a of the electrode 22 are adjacent. The high density regions P of the particle groups are formed in parallel to the electrode pieces 21a and 22a and formed repeatedly with a pitch twice as wide as disposition pitch of the electrode pieces 21a or 22a. And the diffraction grating is generated by the plural high density regions P of the particle groups. If the voltage is stopped to apply to the electrode pair 2, for example, in the generated state of the diffraction grating, the particles start to diffuse and spatial density of the particle groups in the sample becomes homogeneous, and the diffraction grating by the density distribution of the particle groups disappears as a result.

Figure 8:
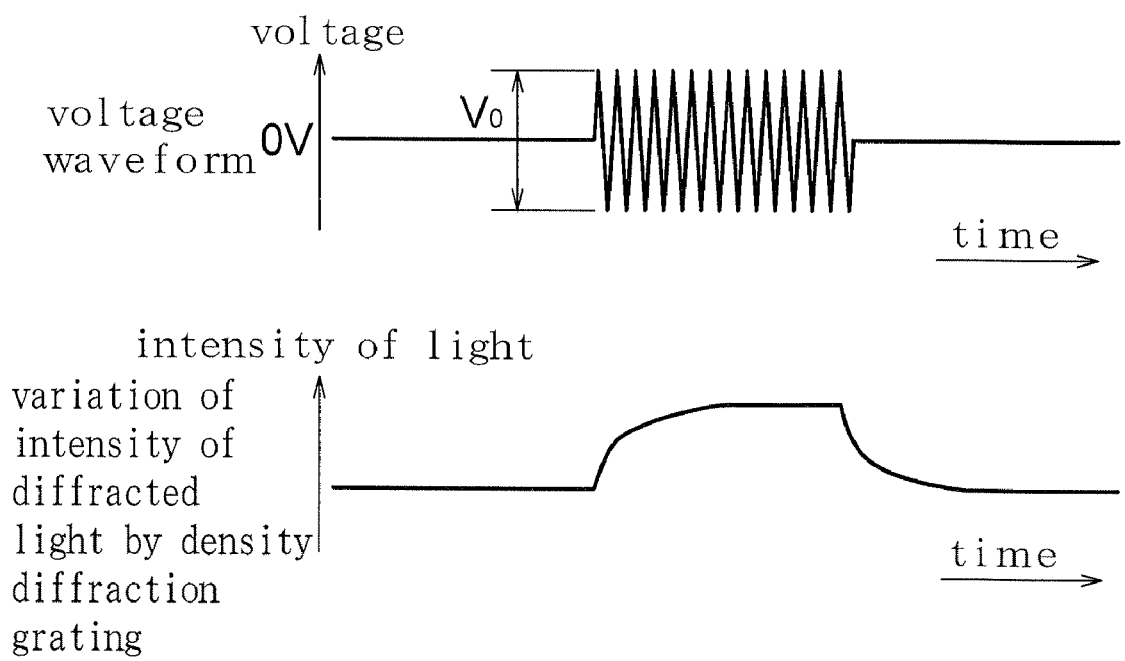
FIG. 8 is a graph showing an example of a temporal variation of a voltage waveform applied to the electrode pair 2 and the intensity of diffracted light by the diffraction grating generated by a density distribution of particle groups, in the embodiment of the present invention.

By irradiating a beam of light from the irradiation optical system 5 to the diffraction grating by the density distribution of the particle groups, this beam of light receives a diffraction by the diffraction grating, and the intensity of diffracted light weakens gradually in the disappearing process of the diffraction grating. FIG. 8 graphs examples of a temporal variation of waveform of voltage applied to the electrode pair 2 and that of the intensity of diffracted light by the diffraction grating formed by the density distribution of the particle groups. In the examples, sinusoidal alternate voltage with a constant voltage $V_0$ is applied to the electrode pair 2 to give the particles a dielectrophoretic force to generate a diffraction grating and then application of the voltage is stopped to stop the dielectrophoretic force.

Because the temporal variation of the intensity of diffracted light in this disappearing process of the diffraction grating by the density distribution of the particle groups depends on the diffusion coefficient of the particles, the diffusion coefficient D of the particles in the sample can be obtained from the measurement result of the temporal variation. On the other hand, the diffusion coefficient D of the particles in the liquid is represented by the following Einstein-Stokes relation $$D = K_B T / 3\pi \eta d$$

wherein $K_B$ is Boltzmann constant, T is absolute temperature of liquid, $\eta$ is viscosity of liquid, and d is particle size.

If the diffusion coefficient D of the particles can be obtained from the result of temporal variation of the intensity of diffracted light in the disappearing process of the density distribution grating measured by the above apparatus, the particle size d of unknown particle groups can be calculated. Or if the above measurement is performed with diffusing known monodispersed particle groups in a liquid with unknown viscosity $\eta$, the viscosity of the liquid can be obtained.

The approximate analysis expression showing the relation between the temporal variation of the measured intensity of diffracted light and the diffusion coefficient of the particles is as shown in the above formula (25). However, this analysis expression can give a correct diffusion coefficient in the case that the above condition of $\phi$, $\mu << 1$ is satisfied, as already mentioned.

And if particle groups with unknown particle size is dispersed in a liquid to measure particle size of the particle groups, samples having different degrees of dilution are prepared: the samples being suspension liquid prepared by diluting the particle groups to be measured in the liquid, density diffraction gratings are formed on same dielectrophoretic condition, and temporal variation of intensity of diffracted light is measured for each concentration. Attenuation characteristic of diffracted light between beginning of diffusion of the density diffraction grating and disappearance of the diffracted light generated by the density diffraction grating for respective measured results is compared among samples from a low concentration sample to a high concentration sample, when there are data which does not coincide with the characteristic on the high concentration side, the diffusion coefficient D is obtained from data in concentration area which coincide with the characteristic, and the obtained result D is applied to the Einstein-Stokes relation, analysis of particle size of the particle groups to be measured can be consequently performed.

And, as other method, if a sample in which particle groups to be measured with unknown particle size are dispersed in the liquid is measured, applied voltage or application time among dielectrophoretic conditions is changed while the density diffraction grating is formed, and temporal variation of intensity of diffracted light is measured under each of the dielectrophoretic conditions. Attenuation characteristic of diffracted light between beginning of diffusion of the density diffraction grating and disappearance of the diffracted light generated by the density diffraction grating is compared with the measured results, when there are data which does not coincide with the characteristic on the side of the strong dielectrophoretic condition (high voltage or long time voltage application), particle size analysis described above is performed from the data in the condition area which coincides with the characteristic.

Further, as other method, when a sample in which particle groups to be measured with unknown particle size are dispersed in the liquid is measured, applied voltage or application time of voltage among dielectrophoretic conditions is changed while the density diffraction grating is formed, and temporal variation of intensity of diffracted light is measured under each of the dielectrophoretic conditions. Attenuation characteristic of diffracted light between beginning of diffusion of the density diffraction grating and disappearance of the diffracted light generated by the density diffraction grating is compared with the measured results, when there are data which does not coincide with the characteristic on the side of the strong dielectrophoretic condition (high voltage or long time voltage application), particle size analysis described above is performed without using the data of the initial diffusion which is the strong dielectrophoretic condition.

Figure 9A:
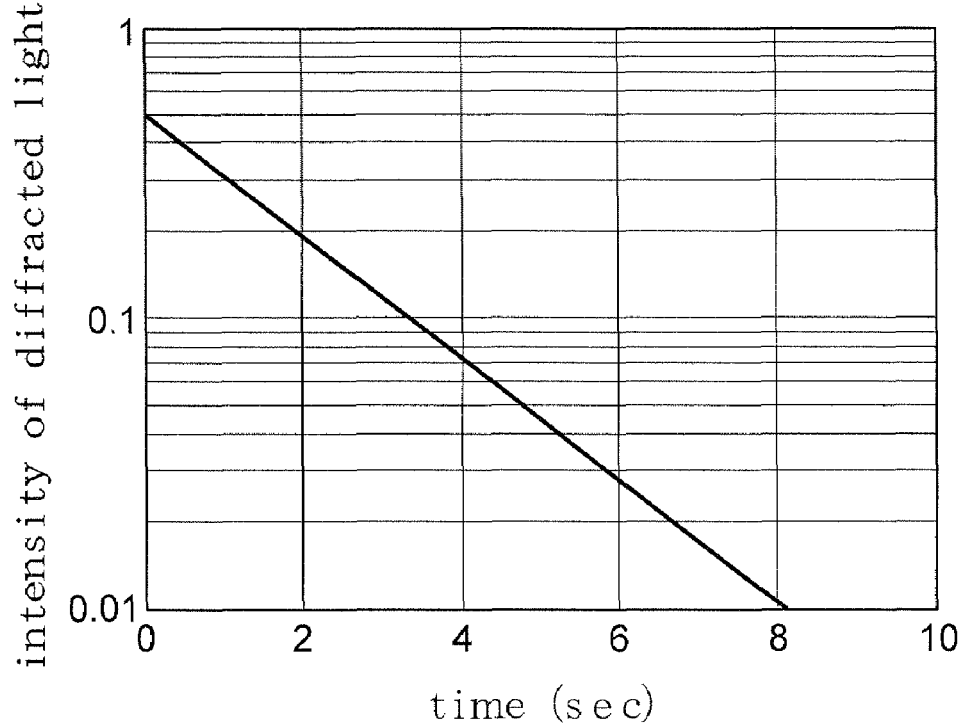
FIG. 9(A) shows a characteristic when measuring a monodispersed particle groups.
Figure 9B:
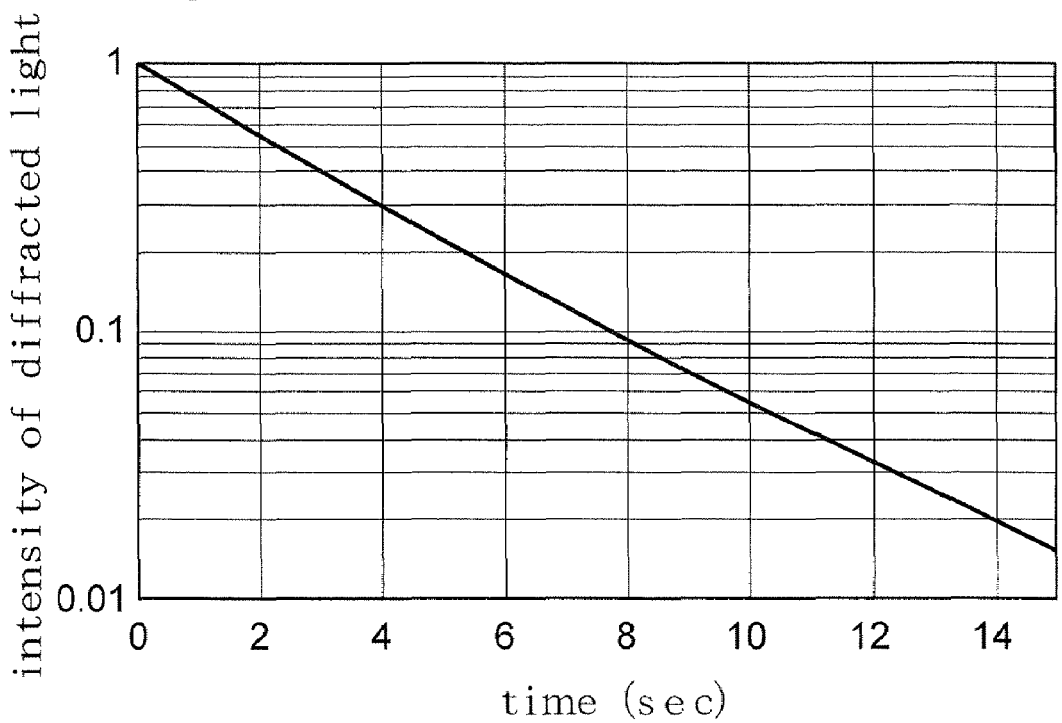
FIG. 9(B) shows a characteristic when measuring the particle groups having mixed particle sizes.

According to the particle size analysis using the formula (25), if particle sizes of particle groups to be measured have distribution, the distribution can be found. FIG. 9 illustrates an example thereof. FIG. 9(A) graphs attenuation characteristic of diffracted light when monodispersed particle groups with uniform particle size are measured, and FIG. 9(B) graphs as an extreme example attenuation characteristic of diffracted light when measured particle groups is composed of particle sizes 50 µm and 100 µm. As clear from a comparison of these graphs, the attenuation characteristic of diffracted light becomes a straight line on a semi-logarithmic graph if the particle size is uniform. However if the particle size is not uniform, the attenuation characteristic becomes downward-convex curve on the semi-logarithmic graph. Distribution of particle size in the particle groups to be measured can be found from the characteristic shown by the graph, and it consequently becomes possible to separate the influence thereof.

In case of obtaining the viscosity of a liquid, monodispersed particles with known particle size is dispersed in liquid to be measured as above described, same measurement as the example described above is performed to obtain attenuation characteristic of diffracted light, diffusion coefficient D is obtained from the result using the formula (25), and the diffusion coefficient D obtained by the above measurement is applied to the above Einstein-Stokes relation on the condition that the particle size d is known and the viscosity η is unknown. The viscosity η can be consequently calculated.

INDUSTRIAL APPLICABILITY

According to the present invention, particle size of particle groups to be measured can be analyzed from temporal variation of intensity of transient diffracted light by particle concentration variation associated with diffusion inside a density diffraction grating, moreover it becomes possible to separate influence of distribution of particle size, and more precise analysis consequently becomes possible. Owing to the simple analysis formulae, it is possible to shorten time required for multivariate analysis in viscosity analysis. Further, in case of measuring viscosity of a liquid, time required for the analysis can be shortened by the simple analysis formulae.

I claim:

1. A method of analysis in an optical measuring method, wherein the optical measuring method uses an apparatus comprising:

a container that retains a gel sample or a liquid formed by dispersing particle groups movably in a medium;

a power supply that generates a voltage with a predetermined pattern including a direct current, frequency modulation and voltage modulation, or pattern capable of being arbitrarily set;

an electrode pair provided in the container, which generates a regularly lined electric field distribution in the container by applying the voltage from the power supply;

a control means that controls application of the voltage from the power supply to the electrode pair to control generation of a diffraction grating generated by density distribution of particle groups in the sample inside the container generated by dielectrophoretic force acting on the particle groups and disappearance thereof;

a light source that irradiates beam of light to an area where the diffraction grating is generated inside the container; and a photo-detector that detects diffracted light of the beam of light by the diffraction grating, the optical measuring method performing a particle size analysis of the particle groups in the sample from a temporal variation of intensity of a diffracted light detected by the photo-detector, wherein the method of analysis, comprising the step of:
using the Einstein-Stokes relation, $$D = K_B T / 3\pi \eta d,$$

wherein $K_B$ is a Boltzmann constant as a diffusion coefficient, T is an absolute temperature of the particle-dispersed liquid to be measured, η is a viscosity of the particle-dispersed liquid or the gel to be measured, and d is a particle size of the particles to be measured, and an approximate analysis expression of a diffracted light attenuation, $$I(t) = \propto \exp[-2q^2 Dt],$$

which uses $q = 2\pi/\Lambda$ defined by a particle concentration modulation period $\Lambda$ in the diffraction grating generated by density distribution of the particle groups to obtain the particle diameter d.

2. A method of analysis in an optical measuring method according to claim 1, further comprising:

measuring a plurality of samples having various concentrations under same dielectrophoretic condition in the measurement;

comparing the measurement results to extract a concentration condition in which a phase modulation amplitude of the diffraction grating generated by the density distribution of the particle groups with respect to incident light is smaller than 1 and an amplitude modulation amplitude thereof is smaller than 1; and applying the approximate analysis expression of the diffracted light attenuation to the result measured under the extracted concentration condition.

3. A method of analysis in an optical measuring method according to claim 1, further comprising:

applying the approximate analysis expression of the diffracted light attenuation to a diffracted light signal only in a time domain in which a phase modulation amplitude of the diffraction grating generated by the density distribution of the particle groups with respect to incident light is smaller than 1 and an amplitude modulation amplitude thereof is smaller than 1.

4. A method of analysis in an optical measuring method, according to claim 1, wherein the measurement is performed under an voltage application time for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

5. A method of analysis in an optical measuring method, according to claim 1, wherein the measurement is performed under an application voltage for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

6. A method of analysis in an optical measuring method, wherein the optical measuring method uses an apparatus comprising:

a container that retains a gel or a sample liquid formed by dispersing particle groups with known particle size movably in a medium;

a power supply that generates a voltage with a predetermined pattern including a direct current, frequency modulation and voltage modulation, or pattern capable of being arbitrarily set;

an electrode pair provided in the container, which generates a regularly lined electric field distribution in the container by applying the voltage from the power supply;

a control means that controls application of the voltage from the power supply to the electrode pair to control generation of a diffraction grating generated by density distribution of particle groups generated by dielectrophoretic force acting on particles in a suspension inside the container and disappearance thereof;

a light source that irradiates beam of light to an area where the diffraction grating is generated inside the container; and a photo-detector that detects diffracted light of the beam of light by the diffraction grating, the optical measuring method performing a viscosity analysis of the sample liquid and gel from a temporal variation of intensity of a diffracted light detected by the photo-detector, wherein the method of analysis, comprising the step of:

using the Einstein-Stokes relation, $$D=K_B T/3\pi\eta d,$$

wherein $K_B$ is a Boltzmann constant as a diffusion coefficient, T is an absolute temperature of the sample liquid or gel to be measured, $\eta$ is a viscosity of the sample liquid or gel to be measured, and d is a known particle size of the particles, and an approximate analysis expression of a diffracted light attenuation, $$I(t)=\propto\exp[-2q^2 Dt],$$

which uses $q=2\pi/\Lambda$ defined by a particle concentration modulation period $\Lambda$ in the diffraction grating generated by density distribution of the particle groups to obtain the viscosity $\eta$ of the sample liquid or gel.

7. A method of analysis in an optical measuring method according to claim 6, further comprising:

measuring a plurality of samples having various concentrations under same dielectrophoretic condition in the measurement;

comparing the measurement results to extract a concentration condition in which a phase modulation amplitude of the diffraction grating generated by the density distribution of the particle groups with respect to incident light is smaller than 1 and an amplitude modulation amplitude thereof is smaller than 1; and applying the approximate analysis expression of the diffracted light attenuation to the result measured under the extracted concentration condition.

8. A method of analysis in an optical measuring method according to claim 6, further comprising:

applying the approximate analysis expression of the diffracted light attenuation to a diffracted light signal only in a time domain in which a phase modulation amplitude of the diffraction grating generated by the density distribution of the particle groups with respect to incident light is smaller than 1 and an amplitude modulation amplitude thereof is smaller than 1.

9. A method of analysis in an optical measuring method, according to claim 6, wherein the measurement is performed under an voltage application time for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

10. A method of analysis in an optical measuring method, according to claim 6, wherein the measurement is performed under an application voltage for controlling an appropriate dielectrophoretic force such that a phase modulation amplitude of the diffraction grating generated by the density distribution of the particle groups with respect to incident light is smaller than 1 and an amplitude modulation amplitude thereof is smaller than 1.

* * * * *